(12) United States Patent
Kabeya et al.

(10) Patent No.: US 11,423,325 B2
(45) Date of Patent: Aug. 23, 2022

(54) REGRESSION FOR METRIC DATASET

(71) Applicant: INTERNATIONAL BUSINESS MACHINES CORPORATION, Armonk, NY (US)

(72) Inventors: Yoshinori Kabeya, Kanagawa (JP); Emiko Takeuchi, Tokyo (JP); Daisuke Takuma, Tokyo (JP); Hirobumi Toyoshima, Tokyo (JP)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 1149 days.

(21) Appl. No.: 15/793,214

(22) Filed: Oct. 25, 2017

(65) Prior Publication Data

US 2019/0122144 A1    Apr. 25, 2019

(51) Int. Cl.
*G06N 20/00* (2019.01)
*G06F 3/01* (2006.01)
(Continued)

(52) U.S. Cl.
CPC ............. *G06N 20/00* (2019.01); *G06F 3/013* (2013.01); *G06N 5/02* (2013.01); *G10L 15/00* (2013.01);
(Continued)

(58) Field of Classification Search
CPC .......... G06N 20/00; G06N 5/02; G16H 10/60; G16H 50/20; G16H 50/50; G06F 3/013;
(Continued)

(56) References Cited

U.S. PATENT DOCUMENTS

| 7,929,730 B2 | 4/2011 | Huang et al. |
| 8,886,581 B2 | 11/2014 | Frank et al. |

(Continued)

FOREIGN PATENT DOCUMENTS

| CN | 106685674 A | 5/2017 |
| CN | 106779230 A | 5/2017 |

(Continued)

OTHER PUBLICATIONS

Subasi et al., Classification of EEG Signals Using Neural Network and Logistic Regression, Computer Methods and Programs in Biomedicine (2005), vol. 78, Issue 2, pp. 87-99, May 2005. (Year: 2005).*

(Continued)

*Primary Examiner* — Brian M Smith
*Assistant Examiner* — Marshall L Werner
(74) *Attorney, Agent, or Firm* — Tutunjian & Bitetto, P.C.; Randall Bluestone

(57) ABSTRACT

A method, a system, and a computer program product for predicting an outcome expected for a particular positional value is provided. In the method, an input set of data records, each having a label and a positional value, and a target positional value are obtained. The label of each data record is one in a label set. A learning model that includes an output layer, an input layer corresponding to the label set and a network structure provided therebetween is read. In the learning model, the network structure has a plurality of functions trained so as to evaluate influence from each label in the label set depending on a relationship between the target positional value and a representative positional value associated with the label in the label set. A target outcome is estimated for the target positional value from the input set using the learning model.

24 Claims, 11 Drawing Sheets

(51) Int. Cl.
  *H04L 9/40* (2022.01)
  *G06N 5/02* (2006.01)
  *G16H 10/60* (2018.01)
  *G10L 15/00* (2013.01)
  *G16H 50/50* (2018.01)
  *G16H 50/20* (2018.01)

(52) U.S. Cl.
  CPC ............ *G16H 10/60* (2018.01); *G16H 50/20* (2018.01); *G16H 50/50* (2018.01); *H04L 63/1408* (2013.01); *H04L 63/1425* (2013.01); G06T 2207/20081 (2013.01)

(58) Field of Classification Search
  CPC . G10L 15/00; H04L 63/1408; H04L 63/1425; G06T 2207/20081
  See application file for complete search history.

(56) References Cited

U.S. PATENT DOCUMENTS

| | | | |
|---|---|---|---|
| 9,319,421 | B2 | 4/2016 | Ferragut et al. |
| 10,061,383 | B1 * | 8/2018 | Ludusan ............... G06F 1/1626 |
| 2013/0006915 | A1 | 1/2013 | Gunawardana et al. |
| 2014/0006324 | A1 | 1/2014 | Doug et al. |
| 2015/0339680 | A1 | 11/2015 | Takahashi |
| 2017/0249549 | A1 | 8/2017 | Bai |

FOREIGN PATENT DOCUMENTS

| | | | | |
|---|---|---|---|---|
| WO | 2017069743 | A | 4/2017 | |
| WO | WO-2019018879 | A1 * | 1/2019 | ............... A61B 5/00 |

OTHER PUBLICATIONS

Friedman et al., Additive Logistic Regression: A Statistical View of Boosting, The Annals of Statistics, vol. 28, No. 2, pp. 337-407, 2000. (Year: 2000).*
Fotheringham et al., Geographical and Temporal Weighted Regression (GTWR), Geographical Analysis, pp. 1-22, 2015. (Year: 2015).*
Song et al., Modeling Fire Occurrence at the City Scale: A Comparison Between Geographically Weighted Regression and Global Linear Regression, International Journal of Environmental Research and Public Health, vol. 14, Issue 4, pp. 1-23, Apr. 2017. (Year: 2017).*
Gunawardana, "A Model for Temporal Dependencies in Event Streams", NIPS, 2011, pp. 1-9.
Hochreiter, "Long Short-Term Memory", Neural Computation 9(8), 1997, pp. 1735-1780.
Jiang, "An Improved Geographically and Temporally Weighted Regression Model with Novel Weight Matrix", 12th International Conference on GeoComputation, 2013, pp. 1-6.
Sontag, "VC Dimension of Neural Networks", Neural Networks and Machine Learning, 1998, pp. 1-26.
International Search Report issued in PCTIB2018057754 dated Jan. 21, 2019, 10 pages.

* cited by examiner

REGRESSION FOR METRIC DATASET

BACKGROUND

Technical Field

The present disclosure, generally, relates to machine learning, more particularly, to techniques for predicting an outcome expected for a particular positional value from a set of data records having positional information, by using a machine learning model.

Description of the Related Art

Machine learning on bag-of-words vector data has been one of the most successful technologies in the cognitive computing. Its applications include automation of insurance assessment, call log categorization and other tasks of text analysis, to name but a few.

Recently, demand for learning more complicated data structure has arisen due to expansion of target data for analysis. Such data structure may include electronic medical records, speech texts recognized by ASR (Automatic Speech Recognition) systems, etc., both of which may have a set of data records with respective positional values such as timestamps. The timestamps of the event is useful information to predict an event that is expected to occur at a particular time (e.g. a point in the future) since some events have an influence on a whole sequence while other events have an influence within a certain range (e.g. a few days).

With respect to analysis concerning positional information, geographically and temporally weighted regression (GTWR) with a new weight function that combines the space-time distance and the distance in the factors space has been proposed (R. Jiang, et al. An Improved Geographically and Temporally Weighted Regression Model with a Novel Weight Matrix. Proceedings of the 12th International Conference on GeoComputation, 2013.). While the technique proposed in this literature can consider the location of one sample, however, it is not possible to adapt to a situation where positional information is given for each explanatory variable in one sample. For example, the technique in this literature could not handle the electric medical records, which is a list of events each having a corresponding timestamp.

With respect to analysis concerning positional information, the Piecewise-Constant Conditional Intensity Model, which is a model for learning temporal dependencies in event streams, has been also proposed (A. Gunawardana, et al. A Model for Temporal Dependencies in Event Streams. Advances in Neural Information Processing Systems, 1962—1970, 2011.). In this literature, a closed-form Bayesian approach to learning these models is described. Also an importance sampling algorithm for forecasting future events using these models using a proposal distribution based on Poisson superposition is described. However, since the contribution from occurrence of a certain event on occurrence provability of other event is incorporated into the constant part in the piecewise-constant conditional intensity functions, it is not possible to incorporate, into the model, hypotheses that the contribution on occurrence probability decays over time. Furthermore, even though some parameters related to uncorrelated attributes can be removed, the number of parameters of the model increases basically in the order of the square of the number of attributes.

What is needed is computer-implemented methods, associated computer systems and computer program products, capable of predicting an outcome expected for a particular positional value efficiently from data records with respective positional values.

SUMMARY

According to an embodiment of the present invention, there is provided a computer-implemented method for predicting an outcome expected for a particular positional value. The method includes obtaining an input set of data records and a target positional value, in which each data record has a label and a positional value and the label of each data record is one in a label set. The method also includes reading a learning model that includes an output layer, an input layer corresponding to the label set and a network structure provided therebetween. The network structure has a plurality of functions that are trained so as to evaluate influence from each label in the label set depending on a relationship between the target positional value and a representative positional value associated with the label in the label set. The method further includes estimating a target outcome for the target positional value from the input set using the learning model.

According to the method of the embodiment of the present invention, it is possible to predict the target outcome expected for the target positional value efficiently with taking positional information obtained from the data records into account.

In a preferable embodiment, each function is parameterized by a positional parameter and a weight parameter for a corresponding label in the label set, where the positional parameter represents a range of influence from the corresponding label on the target outcome and the weight parameter presents a magnitude of the influence from the corresponding label on the target outcome. By introducing the positional parameter in addition to the weight parameter, the scale of the influence from the corresponding label can be incorporated into the learning model.

In other preferable embodiment, the function is monotonic to the positional parameter. The monotonicity of the function to the positional parameter makes it easier for the parameters to converge to an optimal.

In further other preferable embodiment, the relationship is a difference or distance between the representative positional value and the target positional value, and the function is monotonic to the difference or the distance. Thereby, the number of the parameters in the learning model is almost linear to the number of the labels in the label set.

In another preferable embodiment, the method further includes preparing a collection of training data, which includes a set of data records each having a label and a positional value, a given positional vale; and an answer given for the given positional value. In the method, the positional parameter and the weight parameter are trained by using the collection of the training data. The rapid learning of the learning model can be expected. In the other words, the amount of training data required for learning can be reduced.

In another preferable embodiment, the method further includes outputting the trained positional parameter as an effective range of the corresponding label to affect the target outcome. Thereby, operators can be informed some knowledge about the scale of the influence from the label.

In one embodiment, the positional value and the target positional value represent a time and a target time, respectively. Each label represents an event. The target outcome is estimated as a probability that a target event is observed at the target time.

In other embodiment, the positional value and the target positional value represent a location and a target location, respectively. Each label represents an object. The target outcome is estimated as a probability that a target result is observed at the target location.

Computer systems and computer program products relating to one or more aspects of the present invention are also described and claimed herein.

According to other embodiment of the present invention, there is provided a computer-implemented method for predicting an outcome expected for a particular positional value. The method includes obtaining an input set of data records and a target positional value, in which each data record has a label and a positional value. The method also includes generating an input vector from the input set. The input vector includes a plurality of elements that represents labels observed in the input set. The elements are associated with representative positional values. The method further includes calculating a degree of influence from each label observed in the input set for the target positional value in a manner based, at least in part, on the elements and the representative positional values associated therewith. The method includes further computing a target outcome for the target positional value based on the degree of influence from each label observed in the input set.

According to the method of the other embodiment of the present invention, it is possible to predict the target outcome expected for the target positional value efficiently with taking positional information obtained from the data records into account.

According to further other embodiment of the present invention, there is provided a computer-implemented method for learning a learning model that is used for predicting an outcome expected for a particular position. The method includes preparing a collection of training data, each of which includes a set of data records, a given positional value and an answer given for the given positional value. Each data record has a label and a positional value and the label of each data record is one in a label set. The method also includes initializing a learning model that includes an output layer, an input layer corresponding to the label set and a network structure provided therebetween. The network structure has a plurality of functions to evaluate influence from each label in the label set depending on f relationship between the given positional value and a representative positional value associated with each label in the label set. The method further includes estimating an outcome for the given positional value from the set of data records in each training data using the learning model. The method includes further updating the plurality of the functions of the learning model by comparing the answer in each training data with the outcome estimated for the given positional value.

According to the method of the further other embodiment of the present invention, it is possible to train the learning model so as to predict the target outcome expected for the target positional value efficiently with taking positional information obtained from the data records into account. The rapid learning of the learning model can be expected. In the other words, the amount of training data required for learning can be reduced.

According to further other embodiment of the present invention, a computer program product for predicting an outcome expected for a particular position. The computer program product includes a computer readable storage medium having a data structure embodied therewith, the data structure readable by a computer. The data structure includes an input layer configured to receive an input vector that includes a plurality of elements. The elements represents labels observed in an input set of data records and are associated with representative positional values obtained from the data records. The data structure includes a network structure connected to the input layer, which has a plurality of functions trained so as to evaluate influence from each label depending on a relationship between the target positional value and a representative positional value associated with each label. The data structure includes further an output layer on top of the etvork structure. The output layer is configured to estimate a target outcome for the target positional value from the input set.

According to the computer program product of the further other embodiment of the present invention, it is possible to predict the target outcome expected for the target positional value efficiently with taking positional information obtained from the data records into account.

Additional features and advantages are realized through the techniques of the present invention. Other embodiments and aspects of the invention are described in detail herein and are considered a part of the claimed invention.

BRIEF DESCRIPTION OF THE DRAWINGS

The following description will provide details of preferred embodiments with reference to the following figures wherein.

DETAILED DESCRIPTION

Now, the present invention will be described using particular embodiments, and the embodiments described hereafter are understood to be only referred to as examples and are not intended to limit the scope of the present invention.

One or more embodiments according to the present invention are directed to computer-implemented methods, computer systems and computer program products for predicting an outcome expected for a particular positional value by using machine learning. Referring to the series of FIGS. 1-11, computer systems and methods for predicting an outcome expected for a particular positional value from a set of data records each having a label and a positional value will be described.

First, referring to the series of FIGS. 1-7, a computer system and a method for predicting a target outcome expected for a target positional value in an event sequence analysis system, according to an exemplary embodiment of the present invention, will be described, in which the positional value is a timestamp representing a time, each label represents an event and the target outcome is estimated as a probability that a target event is observed at a target time. Then, referring to the series of FIGS. 8-9, a computer system and a method for predicting a target outcome expected for a target positional value in a geographical data analysis system, according to other exemplary embodiment of the present invention, will be described, in which the positional value is a geographical point representing a location, each label represents an object, and the target outcome is estimated as a probability that a target result is obtained at a target location.

Embodiment for Event Analysis System

Figure 1:
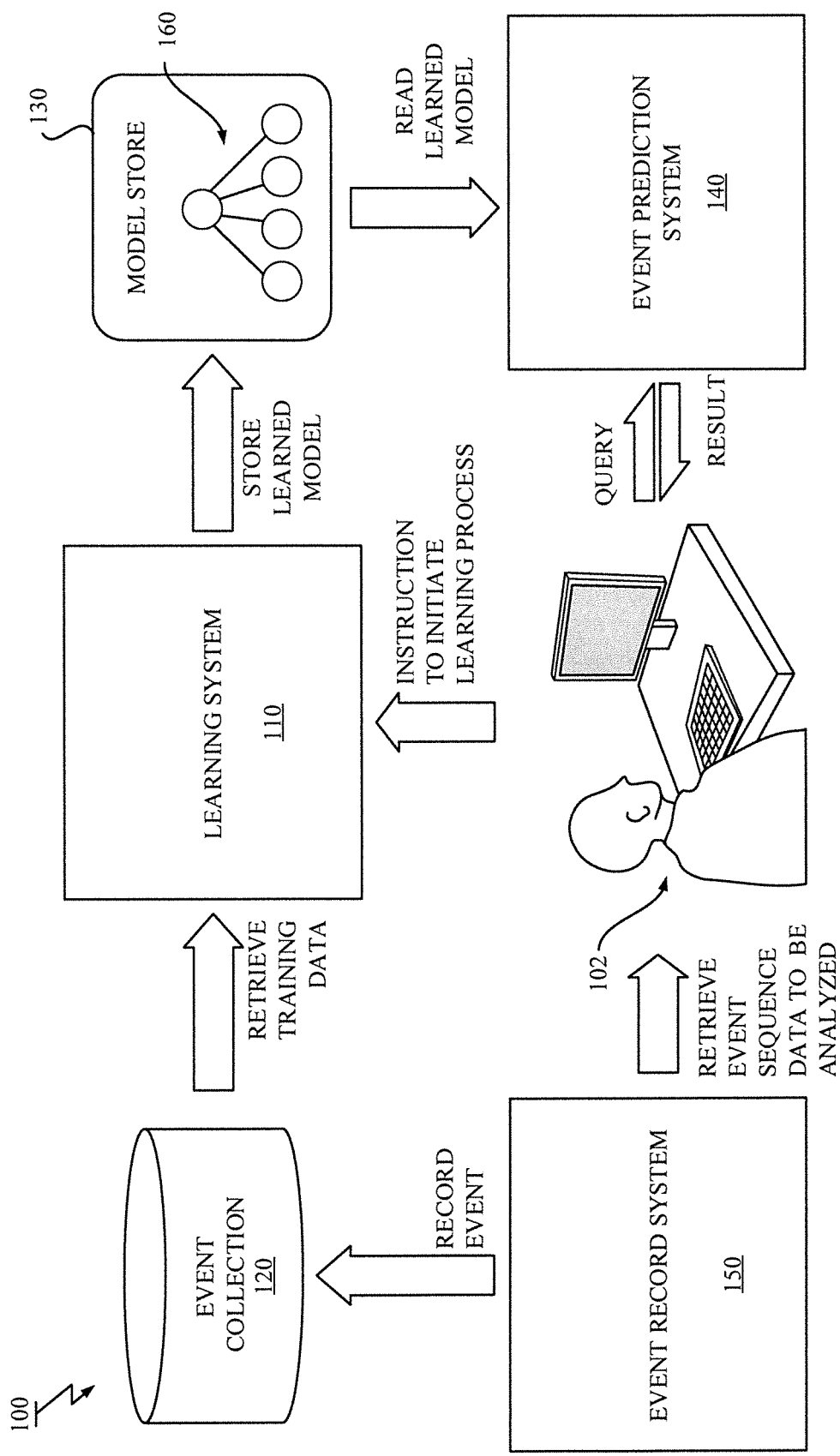
FIG. 1 illustrates a block diagram of an event sequence analysis system according to an exemplary embodiment of the present invention.

With reference to FIG. 1, a block diagram of an event sequence analysis system 100 according to an exemplary embodiment of the present invention is described. As shown in FIG. 1, the event sequence analysis system 100 may include a learning system 110 for learning a machine learning model; an event collection database 120 for storing a collection of event sequence data; a model store 130 for storing the machine learning model trained by the learning system 110; an event prediction system 140 for predicting an event expected for a particular time using the machine learning model stored in the model store 130; and an event record system 150 for recording event information to the event collection database 120. In the described embodiment, the machine learning model that is trained by the learning system 110 and used by the event prediction system 140 is a regression model 160.

The event record system 150 may collect event information originating from one or more event sources, and record the collected event information to the event collection database 120 together with its timestamp as a data record. Such event sources may include, but not limited to, electronic medical record systems, automatic speech recognition (ASR) systems, social networking services, wearable devices, sensor networks, to name but a few.

The event collection database 120 may store a collection of data records on one or more storage media or devices. A set of data records in a certain scope may constitute event sequence data.

Figure 2:
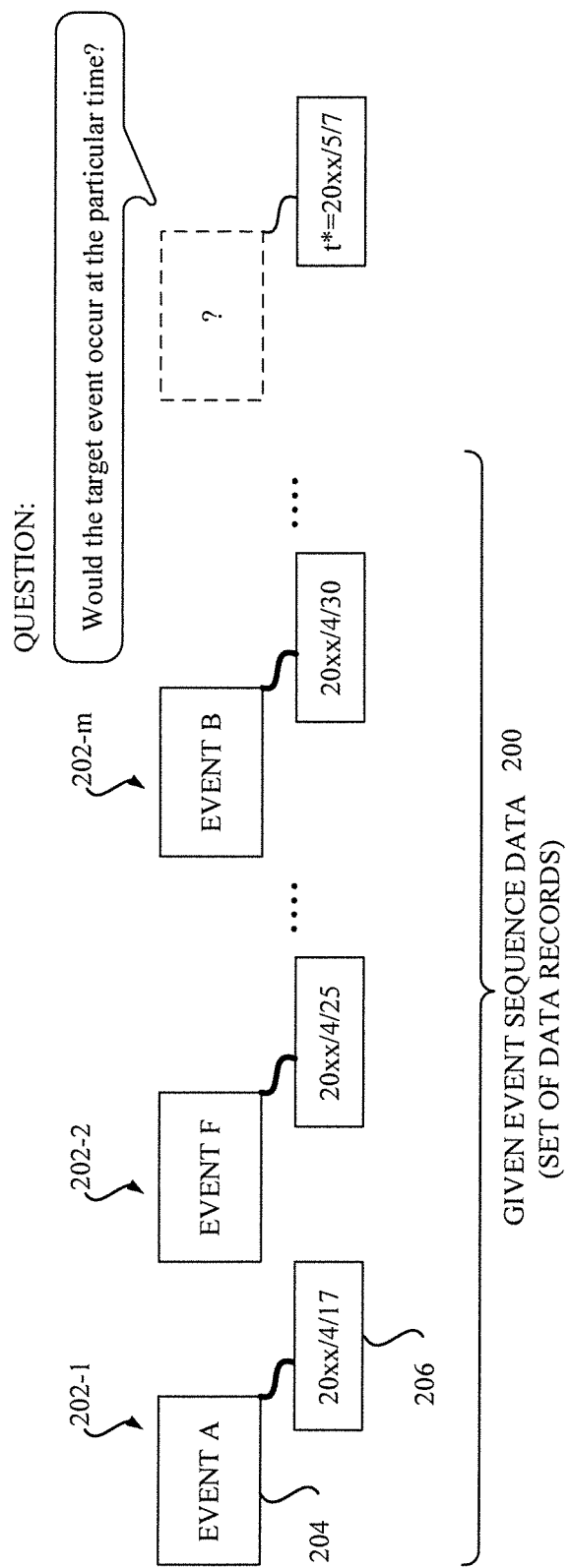
FIG. 2 shows a data structure of event sequence data and a question that the system tries to answer according to the exemplary embodiment of the present invention.

With reference to FIG. 2, an example of a data structure of event sequence data 200 is depicted. As shown in FIG. 2, the event sequence data 200 has a set (or list) of data records 202 (e.g., 202-1, 202-2, . . . , 202-*m*), each of which has a label 204 representing an event and a timestamp 206 representing a time of occurrence of the event. The timestamp 206 is a kind of positional information, and used as a positional value in the described embodiment. Instead of using the timestamp, a serial number representing sequence of occurrence of events may also be used. A predetermined label set is given for the system 100 and the label 204 contained in each data record 202 is one in the predetermined label set. Example of such event sequence data may include electronic medical records in hospitals, speech texts recognized by an ASR systems, message data in social networking services, etc. For example, medical records of a particular patient within a certain range of time may be treated as one event sequence data.

The label 204 is any type data that can represent a particular event. The label 204 may be a value (or identifier) that represents the particular event. Alternatively, the label 204 may be a key-value pair that represents the particular event. Furthermore, the label 204 may also be a key that represents the particular event together with a paired value. The specific values, key-value pairs and keys may depend on a domain from which the event sequence data has been acquired.

Taking the medical records as an example, the label may be a value "bleeding" in the case where the value describes content of the event. The label may be a key-value pair "symptom=headache", "symptom=slight fever", etc., in the case where the key merely describes a type of an event and the key-value pair describes whole content of the event. Also the label may be a key "Blood glucose level" that is associated with a certain value that represents degree or quantity related to the key (e.g. "high" or "85 mg/dL" for "Blood glucose level") in the case where the key describes content of the event together with the value.

Also the event sequence data 200 is not limited to the electronic medical records. Any kind of event sequence data, including timestamped speech texts recognized by the ASR, timestamped message data in social networking services, timestamped sensor data in sensor network and the like, may be a target of the event sequence analysis.

Referring back to FIG. 1, the learning system 110 is configured to train a regression model 160 by using a collection of training data such that the regression model 160 can predict an event expected for a particular time. The learning system 110 may be configured to receive an instruction for initiating a learning process from an operator (e.g., analyst) 102. In response to receiving the instruction, the learning system 110 may first retrieves a collection of training event sequence data stored in the event collection database 120, which may be designated by the instruction, to prepare a collection of training data. The training data may be prepared for a particular target event, which may be designated by the instruction that includes a target label. The target label may be one in the predetermined label set. Each training data may include a set of data records each having a label and a timestamp, and a pair of an answer label and a target timestamp, in which the answer label is identical to the target label for the positive sample or is not identical to the target label for the negative sample. The learning system 110 trains the regression model 160 for the particular target event by using the training data prepared for the particular target event.

The regression model 160 trained by the learning system 110 may be stored in the model store 130. The model store 130 may store the trained regression model 160 with their parameters in one or more storage media or devices.

The event prediction system 140 is configured to estimate a probability of the target event expected to be observed at a target time from an input set by using the regression model 160 that has already been trained by the learning system 110. The event prediction system 140 may be configured to receive a query for performing a prediction process from an operator 102. The query may include or specify test event sequence data and a target timestamp that represents the target time for analysis. An input set of data records each having a label and a timestamp is prepared from the test event sequence data. The test event sequence data may also be obtained from the event record system 150 or the event collection database 120.

The event prediction system 140 reads the regression model 160 from the model store 130, inputs the input set to the regression model 160 to estimate the probability of the target event expected for the target time and returns a result for the query to the operator 102. With reference to FIG. 2, a question that the event sequence analysis system 100 tries to answer is also illustrated. The prediction in the described embodiment is a task to answer a question like "Would the target event occur at a particular time?".

Furthermore, by preparing plural learning models 160 for respective target labels, the event prediction system 140 can answer a question like "What kind of event would occur at a particular time?" by entering the input set of the data records into the plural learning models 160.

Figure 3:
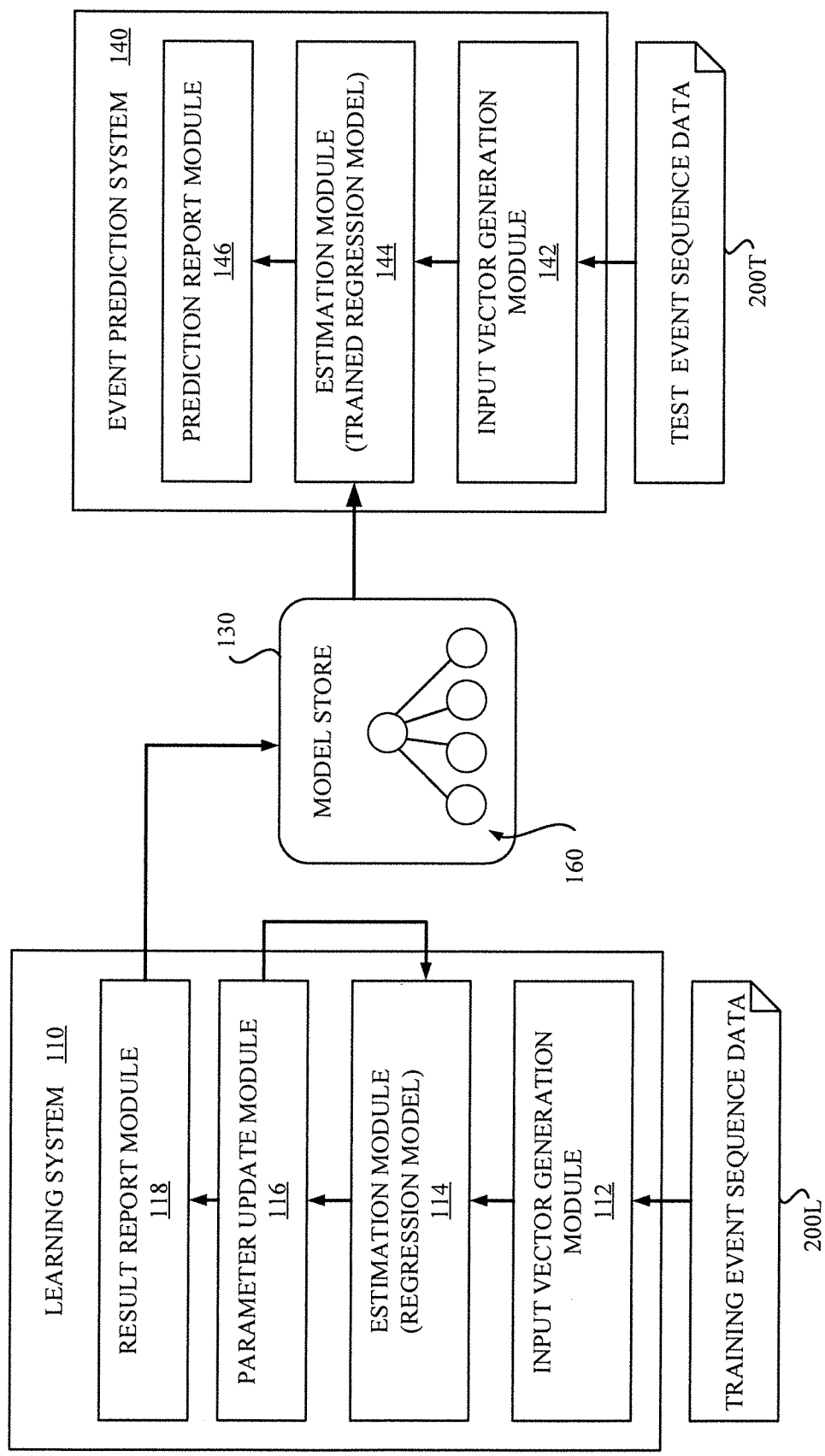
FIG. 3 illustrates detailed block diagrams of a learning system and an event prediction system in the event sequence analysis system according to the exemplary embodiment of the present invention.

With reference to FIG. 3, a detailed block diagram of the learning system 110 in the event sequence analysis system 100 is described. As shown in FIG. 3, the block diagram of the learning system 110 includes an input vector generation module 112 for generating an input vector from each training event sequence data 200L; an estimation module 114 for estimating a probability of the target event for a target time from the input vector by using the regression model 160; a parameter update module 116 for updating parameters of the regression model 160 so as to fit the estimated outcome to the given answer; and a result report module 118 for reporting a result of the learning process.

The input vector generation module 112 may be configured to prepare the training data including the set of the data records each having the label and the timestamp $\{(l_1, t_1), \ldots, (l_m, t_m), \ldots, (l_M, t_M)\}$, and the pair of the answer label and the target timestamp (l*, t*). The training data may include positive samples and negative samples. Each positive sample includes a pair of a label l* that is identical to the target label $l_o$ and observed actually in the training event sequence data 200L (l*=$l_o$) and a target timestamp t* associated with the label l* in the data 200L. Each negative sample includes a pair of a label l* that is not identical to the target label $l_o$ and observed actually in the data 200L (l*≠$l_o$) and a target timestamp t* associated with the label l* (e.g., a case where all patients are subjects to a medical examination, the label l* is set to be positive when the result is positive, and the label l* is set to be negative when the result is negative). Alternatively, a pair of a dummy label that is not observed actually in the data 200L (l*≠$l_o$) and a target timestamp t* that is randomly generated (e.g., in a case where a target event is observed only when the target event occurs actually at a particular time such as occurrence of seizure).

The input vector generation module 112 is configured to generate an input vector $u=(u_1, \ldots, u_N)$ for the regression model 160 from the set of the data records $\{(l_1, t_1), \ldots, (l_m, t_m), \ldots, (l_M, t_M)\}$ in the training data.

Figure 4:
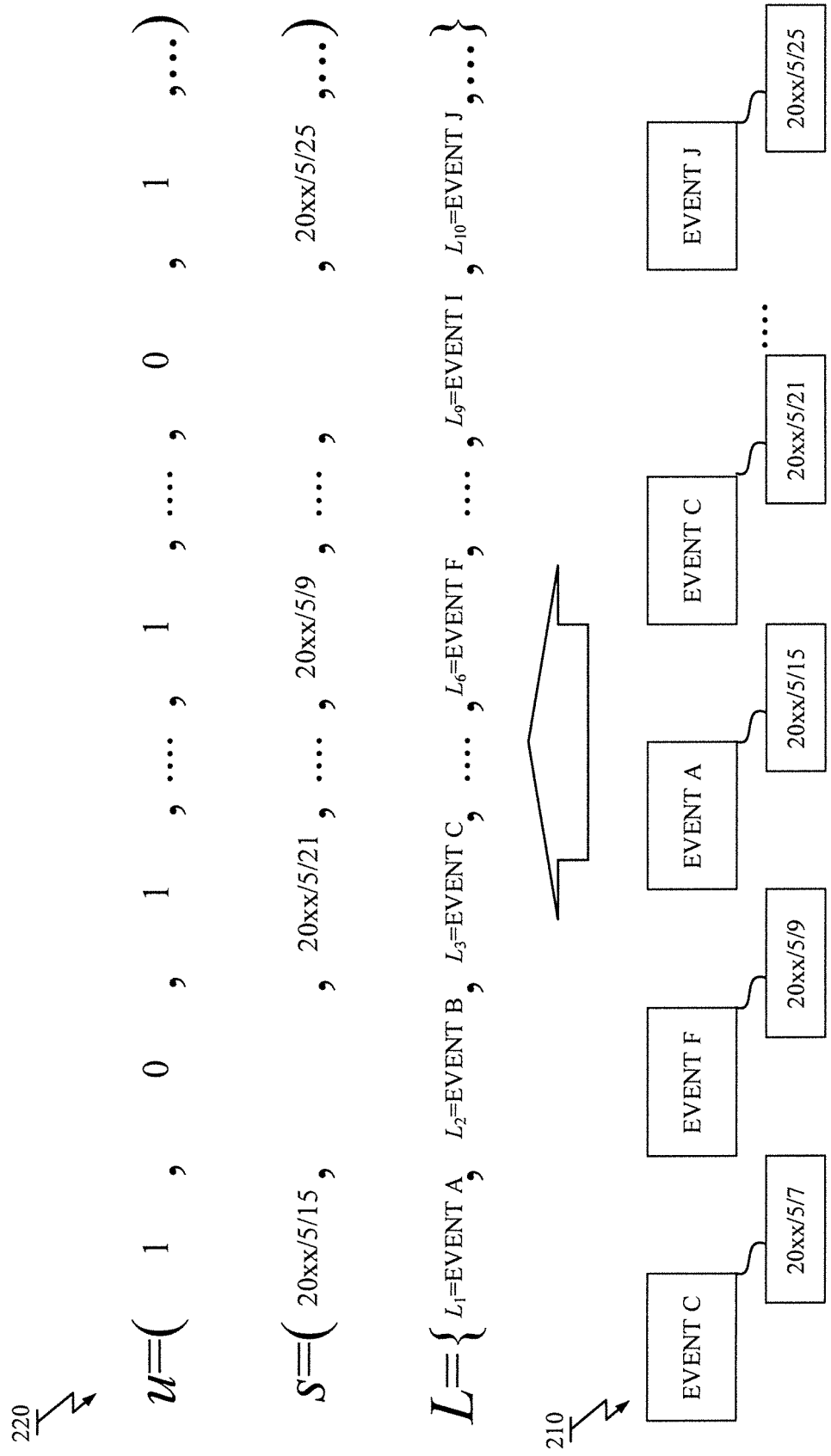
FIG. 4 describes conversion from a set of data records to an input vector by an input vector generation module according to the exemplary embodiment of the present invention.

With reference to FIG. 4, conversion from the set of the data records 210 to the input vector 220 by the input vector generation module 112 is described. In FIG. 4, there is the input vector 220 including a plurality of elements that corresponds to the predetermined label set $L=\{L_1, \ldots, L_N\}$. Each element $u_n$ has a value representing at least whether or not a corresponding label $L_n$ is observed at least once actually in the set of the data records 210. The input vector generation module 112 may set the element $u_n$ by one ($u_n=1$) when the corresponding label $L_n$ exists in the set of the data records $\{l_1, \ldots, l_M\}$. The input vector generation module 112 may set the element $u_n$ by zero ($u_n=0$) when the corresponding label $L_n$ does not exist in the set of the data records $\{l_1, \ldots, l_M\}$.

In one or more embodiment, the value of the element $u_n$ may be set by the value (e.g., 85 [mg/dL]) associated with the key (e.g., Blood glucose level) in the case where the label is a key that describes content of the event together with a value. Also, in other embodiment, the input vector generation module 112 may set the element $u_n$ by a count of appearance of the corresponding label $L_n$ in the set of the data records $\{l_1, \ldots, l_M\}$.

As shown in FIG. 4, each element $u_n$ is associated with a timestamp $t_m$ that may be obtained from one or more data records having the corresponding label $L_n$ in the set of the data records $\{(l_1, t_1), \ldots, (l_m, t_m), \ldots, (l_M, t_M)\}$, as a representative timestamp $s_n$. In a particular embodiment, when the corresponding label $L_n$ appears more than one time, the input vector generation module 112 may select a timestamp $t_m$ closest to the target timestamp t* from among one or more data records having the corresponding label $L_n$. When the corresponding label $L_n$ has not appeared, arbitrary value may be used as the representative timestamp $s_n$. The representative timestamp $s_n$ represents temporal relationship between a time of the data record having the corresponding label ($l_m=L_n$, $t_m$) and a time represented by the target timestamp t*. For given data records ($L_n$, $t_1$), ($L_n$, $t_2$) satisfying $t_1<t_2<t*$, the value $t_2$ is selected as the representative timestamp $s_n$. For example, the representative timestamp $s_3$ corresponding to "EVENT C" is set by "20xx/5/21" from among two records with respective timestamps "20xx/5/7" and "20xx/5/21" as illustrated in FIG. 4. The rule to determine the representative timestamp $s_n$ may not be limited to the rule that selects the timestamp $t_m$ closest to the timestamp t*. Any other rule may be used as long as that can provide a representative timestamp $s_n$ for the element $u_n$ from one or more data records. In other embodiment, a rule that selects the timestamp $t_m$ furthest to the timestamp t* may be employed. In another embodiment, a rule that calculates average of the timestamps in one or more data records having the corresponding label $L_n$ may be employed.

Referring back to FIG. 3, the estimation module 114 is configured to estimate the probability that the target event is observed at the target time, from the input vector 220, which is generated from the input set in each training data, by using the regression model 160 with currently obtained parameters. The estimation module 114 may be configured to initialize the regression model 160 at the beginning of the learning process. The parameters of the regression model 160 may be initialized by appropriate value such as random value. Then, the parameters of the regression model 160 would be iteratively updated by the parameter update module 116 during a course of the learning process.

Figure 5:
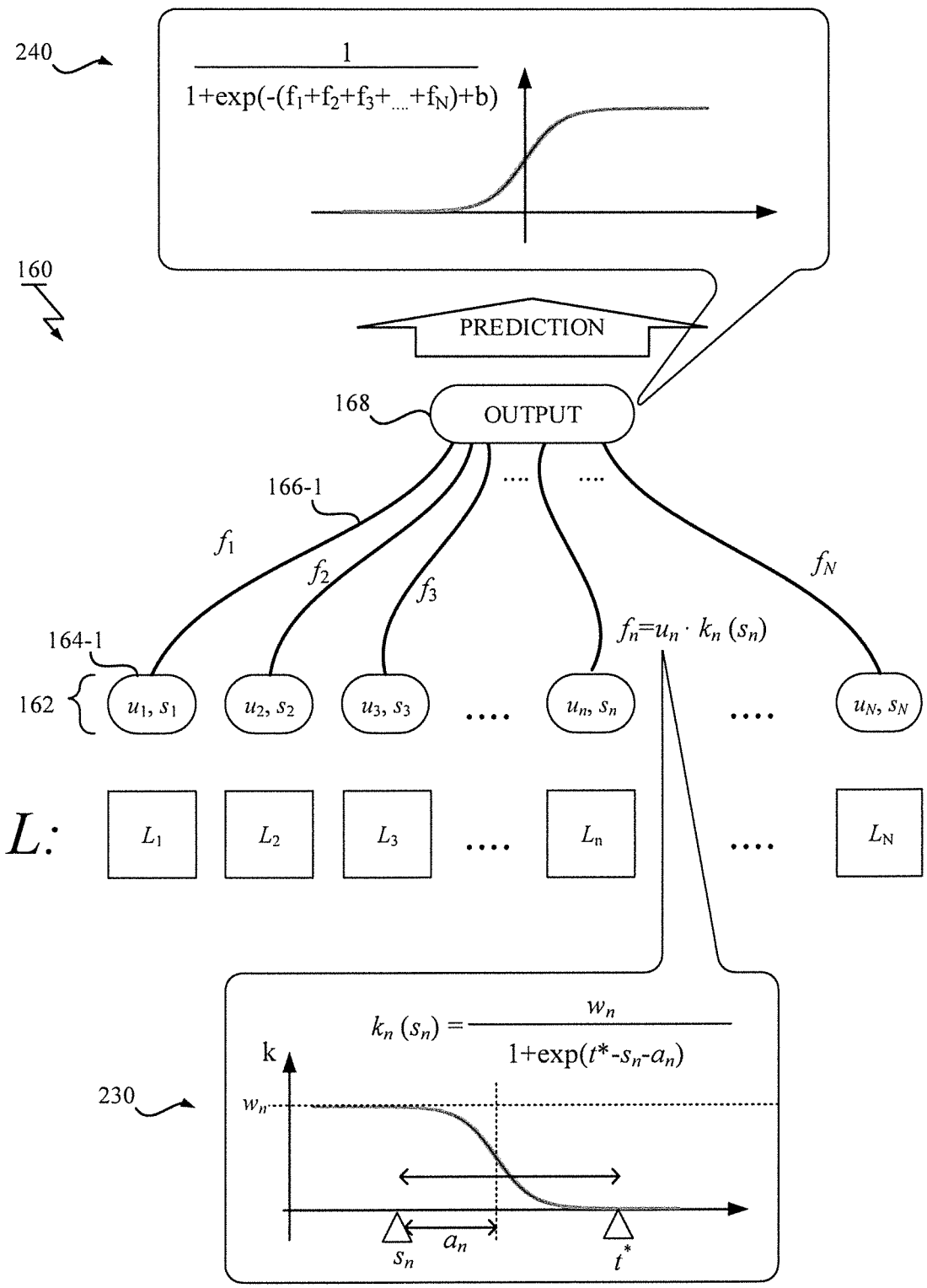
FIG. 5 describes a structure of a regression model used to estimate a probability that a target event is observed at a target time according to the exemplary embodiment of the present invention.

With reference to FIG. 5, a structure of the regression model 160 used to estimate the probability that the target event is observed at the target time is described. As shown in FIG. 5, the regression model 160 includes an input layer 162 corresponding to the predetermined label set L; and an output layer 168 configured to output the probability for a given target timestamp t*; and a network structure provided therebetween.

The input layer 162 is configured to receive the input vector u and the representative timestamps s that are obtained from the set of the data records. In the described embodiment, the input layer 162 includes a plurality of input units 164 each corresponding to a label $L_n$ in the predetermined label set L.

The regression model 160 shown in FIG. 5 is a two layer network model, in which there is one output unit in the output layer 168 and the network structure has a plurality of edges 166, each of which is provided between the corresponding input unit 164 in the input layer 162 and the output unit in the output layer 168.

The network structure may have a plurality of functions $f_n$ (1, ..., N), each of which is trained so as to evaluate influence from each label $L_n$ in the label set L depending on the value of the element $u_n$ corresponding to each label $L_n$ and the representative timestamp $s_n$ associated therewith (more specifically, relationship between the target timestamp t* and the representative timestamp $s_n$). In the described embodiment, each function $f_n$ is assigned to the corresponding edge (e.g. 166-1) between the output unit in the output layer 168 and the input unit (e.g. 164-1) in the input layer 162.

The function $f_n$ computes the input for the output layer 168. The function is represented by a product of the value of the element $u_n$ and a weight calculated by a weight function $k_n$ ($s_n$). Each weight function $k_n$ (subsequently the function $f_n$) is parameterized by a weight parameter $w_n$ and a positional parameter $a_n$. The weight parameter $w_n$ represents magnitude of influence from one label $L_n$ on the target outcome. The positional parameter $a_n$ represents a range of influence from the one label $L_n$ on the target outcome. In a preferable embodiment, the function $f_n$ (=$u_n \cdot k_n$ ($s_n$)) is monotonic for each parameters.

In the described embodiment, the weight function $k_n$ ($s_n$) is represented by following formula:

$$k_n(s_n) = \frac{w_n}{1 + e^{t*-s_n-a_n}}, \quad (1)$$

where the weight function $k_n$ is close to $w_n$ for $t*-s_n < a_n$ and close to 0 for $t*-s_n > a_n$ as indicated by a graph 230 in FIG. 5. In a particular embodiment, it is preferable that polarity of monotonicity of the function $f_n$ (=$u_n \cdot k_n$ ($s_n$)) for each parameter does not change according to the other parameters. Thus, the weight function $k_n$ can be represented by a 4-parameter function expressed as follow:

$$k_n(s_n) = \frac{w_{n+}}{1 + e^{t*-s_n-a_{n+}}} + \frac{w_{n-}}{1 + e^{t*-s_n-a_{n-}}},$$

where $w_{n+} > 0$, $w_{n-} < 0$, $a_{n+} > 0$, and $a_{n-} > 0$. In other embodiment, the weight function $k_n$ may have another parameter that defines the steepness of curve of the function. Such weight function $k_n$ can be represented as follow:

$$k_n(s_n) = \frac{w_n}{1 + e^{c(t*-s_n-a_n)}},$$

where c represents a parameter defining the steepness of the function, which would be also iteratively updated by the parameter update module 116 during the course of the learning process.

In the described embodiment, the weight function $k_n$ is a kind of a sigmoid function that has monotonicity to difference between the target timestamp and the representative timestamp (t*-$s_n$), which represents an assumption that the influence from the event represented by label $L_n$ is monotonic in time. However, in other embodiment, the weight function $k_n$ may be a kind of a bump function that has monotonicity to distance between the target timestamp and the representative timestamp (|t*-$s_n$|), which represents an assumption that the influence from the label $L_n$ has just one peak in time. Thus, a closer event makes a stronger influence on other event. In a particular embodiment with using such bump function, an event that is expected to occur at a particular time, whichever case the particular time is a point in the past or a point in the future, can be predicted.

The output layer 168 on top of the network structure is configured to estimate the probability that a label at target time represented by the target timestamp t* is identical to the target label $l_o$. The output unit in the output layer 168 has an output function that receives a sum of outputs from the plurality of the functions $f_n$ (=$u_n \cdot k_n(s_n)$) to estimate the target outcome. In the described embodiment, the output function is an inverse function of a link function that is a log it function and the target outcome is estimated as a probability that a target event is observed at the target time. In the described embodiment, the output function is represented by following formula:

$$q = \frac{1}{1 + e^{-(f_1+...+f_N)+b}}.$$

where b is a bias parameter, and the output function q is close to 1 for $(f_1+f_2+ ... +f_N) > b$ and close to 0 for $(f_1+f_2+ ... +f_N) < b$ as indicated by a graph 240 in FIG. 5.

Note that the regression model 160 employed in the described embodiment can be seen as an extension of a binary logistic regression model where a binary dependent variable (the target label exists or does not exist) is used and a sigmoid function is used as the output function, which can be used as classifier. However, in other embodiment, the regression model 160 can be generalized to multiclass problems where the dependent variable has more than two categories. Also the output function is not limited to the inverse function of the log it function. In other embodiment, any kind of link functions used in the generalized linear model such as identity function, probit link function, etc., may be used as the output function. In a particular embodiment, the identity function is used as the link function and the target outcome is estimated as an estimated value of an evaluation item (e.g. score, price) for the target time. Also, the regression model 160 is not limited to a two layer network model. In one or more other embodiments, the two layer network model shown in FIG. 5 may be used as a part of other larger network model, in which output of the output layer 168 may be used as an input for an upper structure.

Referring back to FIG. 3, the parameter update module 116 is configured to update the plurality of the functions $f_n$, which is parameterized by the weight parameter $w_n$ and the positional parameter $a_n$, by comparing the answer label (l*=$l_o$ or l*≠$l_o$) in each training data with the probability that a label at target timestamp t* is identical to the target label ($l^*=l_o$). The parameters may be updated by using any standard algorithm. In a particular embodiment, the gradient method with cross-entropy cost function may be used. The weight parameter $w_n$ and the positional parameters $a_n$ (and the bias parameter b) of the regression model 160 would be iteratively updated by the parameter update module 116 so as to minimize the cross-entropy cost function during the course of the learning process.

The result report module 118 is configured to output a result of the learning process in response to the learning process finishing. The result notifies the operator 102 whether or not the learning process has successfully finished. In a preferable embodiment, the result of the learning process may include indication of the positional parameter $a_n$ for each label $L_n$ as an effective range of each label $L_n$ to affect the target outcome. The result report module 118 is also configured to store the regression model 160 with trained parameters in the model store 130.

Further referring to FIG. 3, a detailed block diagram of the event prediction system 140 in the event sequence analysis system 100 is also described. As shown in FIG. 3, the block diagram of the event prediction system 140 includes an input vector generation module 142 for generating an input vector from a test event sequence data 200T; an estimation module 144 for estimating a probability of the target event for a target time from the input vector by using the regression model 160; and a prediction report module 146 for reporting a result of the prediction.

The input vector generation module 142 is configured to receive test event sequence data 200T to obtain an input set of data records and a target positional value $\{(l_1, t_1), \ldots, (l_m, t_m), \ldots, (l_M, t_M)\}$ and $t^*\}$. The input vector generation module 142 may also receive a target label $l_o$. The input vector generation module 142 is further configured to generate an input vector $u=(u_1, \ldots, u_N)$ for the regression model 160 from the input set of the data records $\{(l_1, t_1), \ldots, (l_m, t_m), \ldots, (l_M, t_M)\}$. As similar to the learning system 110, the input vector u includes a plurality of elements $u_n$ corresponding to the predetermined label set $L=\{L_1, \ldots, L_N\}$. Each element $u_n$ has a value representing at least whether or not a corresponding label $L_n$ (in the label set L) is observed actually in the input set of the data records or not. The value of the element $u_n$ may be set by the input vector generation module 142 as same as the learning system 110. The same rule may be used to determine the representative timestamp $s_n$.

The estimation module 144 is configured to read a regression model 160 with the trained parameters from the model store 130 when the estimation module 144 has not yet read the regression model 160 for the target label $l_o$. The estimation module 144 is configured to estimate a probability of a target event for a target time from the input vector, which is generated from the input set, by using the regression model 160.

The prediction report module 146 is configured to output a result of the prediction that may notify the probability that the target event is observed at a target time. The result may include the positional parameter $a_n$ for each label $L_n$ as an effective range of each label $L_n$ to affect the target outcome as supplemental information to help the interpretation of the prediction result.

In particular embodiments, the system 110, 140 and 150, and modules 112~118, 142~146 in the event sequence analysis system 100 described in FIG. 1 and FIG. 3 may be implemented as, but not limited to, a software module including program instructions and/or data structures in conjunction with hardware components; a hardware module including electronic circuitry; or a combination thereof. The modules 110 and its submodules 112~118 described in FIG. 1 and FIG. 3 may be implemented in a single or distributed computer system. The modules 140 and its submodules 142~146 described in FIG. 1 and FIG. 3 may be implemented on the same computer system or other computer system. The event record system 150 may be implemented on a computer system on which the learning system 110 and/or the event prediction system 140 are implemented or other computer system. The event collection database 120 and the model store 130 may be provided by using any internal or external storage device or medium, to which the computer system can access.

Figure 6:
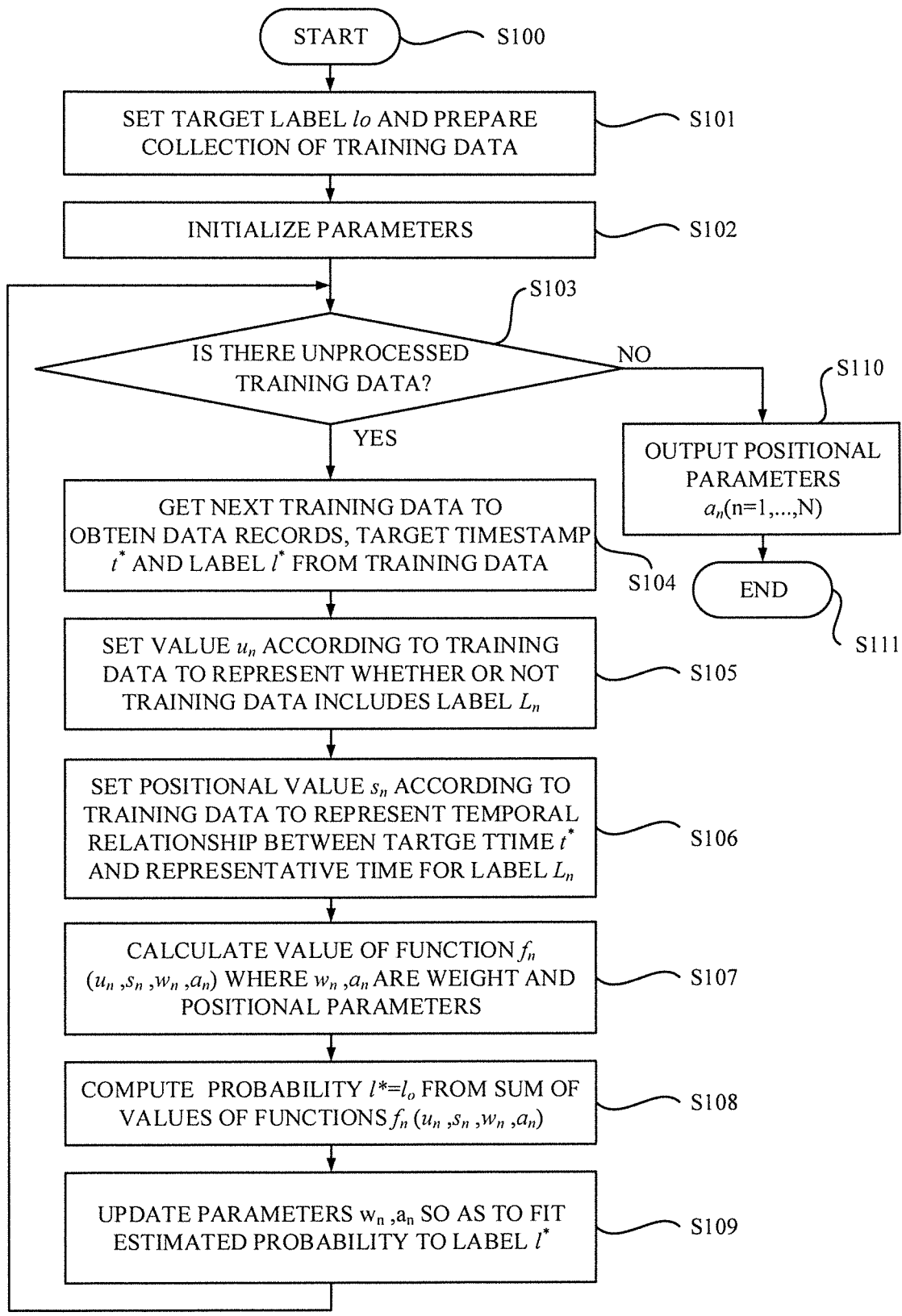
FIG. 6 is a flowchart depicting a learning process for learning the regression model according to an exemplary embodiment of the present invention.

Referring to FIG. 6, a process for learning a regression model 160 according to an exemplary embodiment of the present invention is shown. Note that the process shown in FIG. 6 may be executed by a processing unit that implements the learning system 110 shown in FIG. 1 and FIG. 3.

The process shown in FIG. 6 may begin at step S100 in response to receiving an instruction for initiating a learning process from an operator 102. The operator 102 may designate a collection of event sequence data to be used for training and the target label $l_o$ represents a target event.

At step S101, the processing unit may set the target label $l_o$ and prepare a collection of training data from the collection of the event sequence data. Each training data may include a set of data records each having a label $l_m$ and a timestamp $t_m$, and a pair of an answer label $l^*$ and a target timestamp $t^*$, in which the answer label is identical to the target label ($l^*=l_o$) for the positive sample or is not identical to the target label ($l^{**} \neq l_o$) for the negative sample.

At step S102, the processing unit may initialize the parameters of the regression model 160, which includes the weight parameters $w_n$ and the positional parameters $a_n$, by which the functions $f_n$ are parameterized.

At step S103, the processing unit may determine whether or not there is at least one unprocessed training data to be processed. In response to determining that there is at least one unprocessed training data at step S103, the process may proceed to step S104.

At step S104, the processing unit may get a next training data to obtain a current set of data records $\{(l_1, t_1), \ldots, (l_m, t_m), \ldots, (l_M, t_M)\}$ and a pair of a target timestamp $t^*$ and an answer label $l^*$.

At step S105, the processing unit may set the value of each element $u_n$ according to the current set of the data records $\{l_1, \ldots, l_M\}$ to represent whether or not training data includes each label $L_n$. At step S106, the processing unit may set the positional value $s_n$ associated with the element $u_n$ according to the set of the data records $\{(l_1, t_1), \ldots, (l_m, t_m), \ldots, (l_M, t_M)\}$ to represent the temporal relationship between the target timestamp $t^*$ and the representative timestamp $t_m$ (e.g., closest to $t^*$) for each label $L_n$. By performing the processes of step S105 and S106, the input vector u associated with representative timestamps s is generated as an input for the regression model 160.

At step S107, the processing unit may calculate degree of influence $f_n(u_n, s_n, w_n, a_n)$ from each label $L_n$ for the target timestamp $t^*$ in a manner based on the value of the element $u_n$ and the temporal relationship between the target timestamp $t^*$ and the representative timestamp $s_n$ associated therewith. At step S108, the processing unit may compute the probability that a label at the target timestamp $t^*$ is identical to the target label ($l^*=l_o$) from the sum of the degree of the influence $f_n(u_n, s_n, w_n, a_n)$ from every labels $L_n$ (n=1 . . . , N). By performing the processes of step S107 and S108, an outcome for the given target timestamp $t^*$ may be estimated from the input vector u with representative timestamps s in each training data by using the regression model 160 with currently obtained parameters.

At step S109, the processing unit may update parameters ($w_n$, $a_n$, b) of the regression model 160 so as to fit the estimated probability to actual label 1\* by comparing the answer label in each training data with the outcome estimated for the given target timestamp t\*. In the described embodiment, the gradient method is employed with the cross-entropy cost function. The cross entropy cost function E for given training data i=1, . . . , m may be express as follows:

$$E = \frac{1}{m}\sum_{i=1}^{m}[-p^{(i)}\log q^{(i)} - (1-p^{(i)})\log(1-q^{(i)})]$$

where the $p^{(i)}$ represents a desired output for training data i ($p^{(i)}=1$ if the given $1^*=1_o$, otherwise $p^{(i)}=0$) and $q^{(i)}$ represents an actual output from the output unit for the training data i. The processing unit may calculate partial derivatives of the cost function of the parameters $w_n$, $a_n$, b and updates the weight parameter $w_n$, the positional parameter $a_n$ and the bias parameter b by the partial derivatives as follows;

$$\frac{\partial E}{\partial w_n}, \frac{\partial E}{\partial a_n}, \text{ and } \frac{\partial E}{\partial b}.$$

In order to reduce overfitting, regularization such as L2 regularization can be applied to the cost function E. The example of the cost function with the L2 regularization terms can be express as follow:

$$E = \frac{1}{m}\sum_{i=1}^{m}[-p^{(i)}\log q^{(i)} - (1-p^{(i)})\log(1-q^{(i)})] + \frac{\lambda_w}{2m}\sum_{n=1}^{N}w_n^2 + \frac{\lambda_a}{2m}\sum_{n=1}^{N}a_n^2$$

where $\lambda_w$ and $\lambda_a$ represent regularization parameters for the weight parameter $w_n$ and the positional parameter $a_n$, respectively. In a preferable embodiment, the regularization parameter $\lambda_w$ for the weight parameters $w_n$ is different from the regularization parameter $\lambda_a$ for the positional parameters $a_n$ ($\lambda_w \neq \lambda_a$), this means that the regularization constraint for the weight parameter $w_n$ and the regularization constraint for the positional parameter $a_n$ may have different strength each other.

After the process of step S109, the process may loop back to step S103. In response to determining that there is no unprocessed training data anymore since all prepared training data is processed or a convergence criterion is satisfied at step S103, the process may branch to step S110.

At step S110, the processing unit may output positional parameters $a_u$ (n=1 . . . N) as a result of learning process, and the process may ends at step S111.

Figure 7:
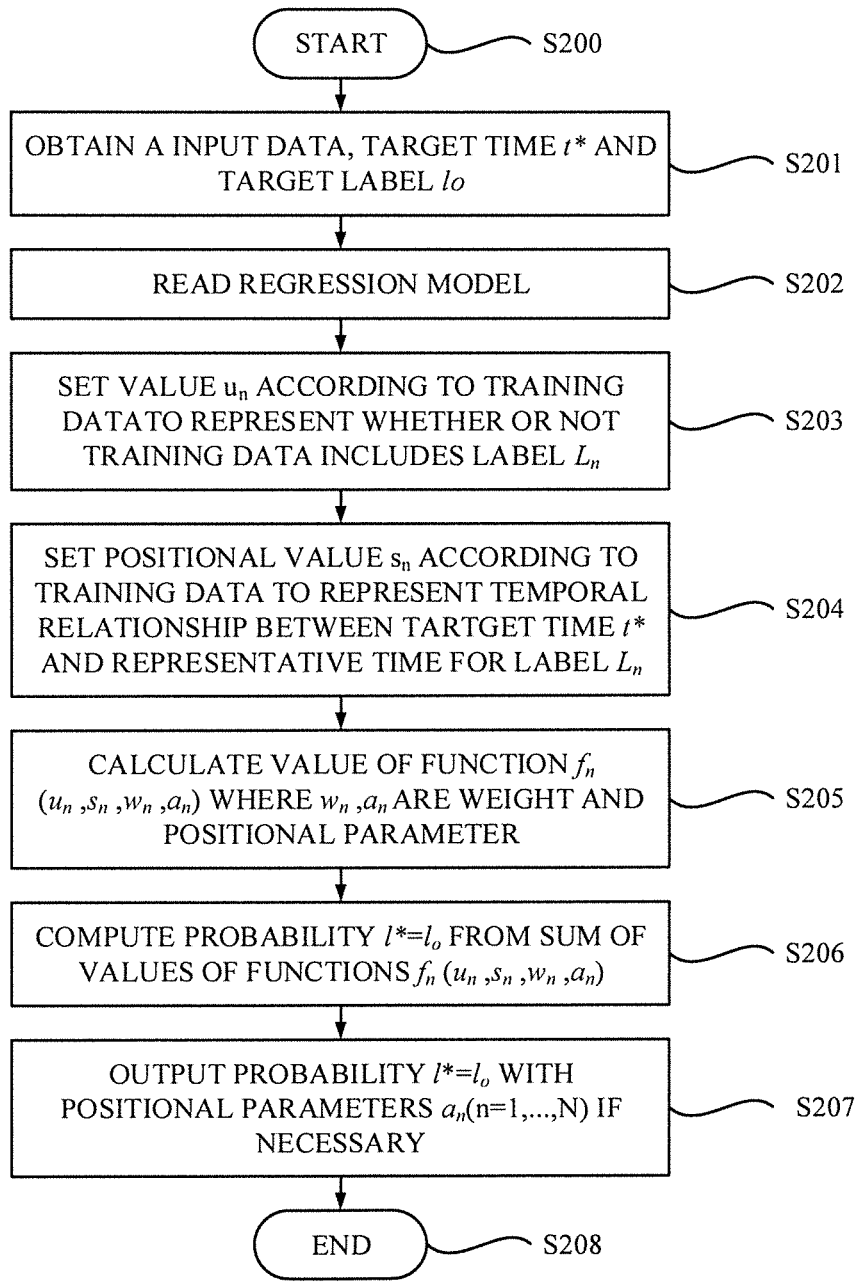
FIG. 7 is a flowchart depicting a prediction process for estimating a probability that a target event is observed at a target time according to an exemplary embodiment of the present invention.

Referring to FIG. 7, a prediction process for estimating a probability that a target event is observed at a target time according to an exemplary embodiment of the present invention is shown. Note that the process shown in FIG. 7 may be executed by a processing unit that implements the event prediction system 140 shown in FIG. 1 and FIG. 3.

The process shown in FIG. 7 may begin at step S200 in response to receiving a query for performing a prediction process from an operator 102. At step S201, the processing unit may obtain an input set of data records $\{(l_1, t_1), \ldots, (l_m, t_m), \ldots, (l_M, t_M)\}$, the target timestamp t\* representing a target time and a target label 1, representing a target event, all or a part of which may be designated by the query.

At step S202, the processing unit may read a regression model 160 for the target label $l_o$ from the model store 130. The regression model 160 may include the weight parameters $w_n$ and the positional parameters $a_n$, by which the functions $f_n$ are parameterized.

At step S203, the processing unit may set the value of each element $u_n$ according to the input set of the data records $\{l_1, \ldots, l_M\}$ to represent at least whether or not the input set includes each label $L_n$. At step S204, the processing unit may set the positional value $s_n$ associated with each element $u_n$ according to the input set of the data records $\{(l_1, t_1), \ldots, (l_m, t_m), \ldots, (l_M, t_M)\}$ to represent the temporal relationship between the target timestamp t\* and the representative timestamp $t_m$ (e.g., closest to t\*) for each label $L_n$. By performing the processes of step S203 and S204, the input vector u with representative timestamps s is generated as an input for the regression model 160.

At step S205, the processing unit may calculate degree of influence $f_n$ from each label $L_n$ for the target timestamp t\* in a manner based on the value of the element $u_n$ and the temporal relationship between the target timestamp t\* and the representative timestamp $s_n$ associated therewith. At step S206, the processing unit may compute the probability that a label at the target timestamp t\* is identical to the target label ($1^*=1_o$) from the sum of the degree of the influence $f_n$ ($u_n$, $s_n$, $w_n$, $a_n$) from every labels $L_n$ (n=1 . . . , N). By performing the processes of step S205 and S206, an outcome for the target timestamp t\* may be estimated from the input vector u with representative timestamps s by using the regression model 160.

At step S207, the processing unit may output the estimated probability ($1^*=1_o$) with the positional parameters $a_u$ (n=1 . . . N) if necessary as a result of the prediction process, and the process may ends at step S208. The positional parameters $a_u$ (n=1 . . . N) may be included in the result as supplemental information to help the interpretation of the prediction result.

Embodiment for Geographical Data Analysis System

In the aforementioned exemplary embodiment, the positional value is the timestamp representing the time, each label represents the event and the target outcome is estimated as the probability of the target event expected to be observed at the target time. However, in one or more other embodiments, the positional value can be generalized to a point in a metric space or topological space T. Note that the topological space may be employed in a case where overall information is given by seaming a plurality of local maps, thus the distance between points across different local maps may not be defined but the monotonicity of the function $f$ and the partial derivatives of the parameters can be defined (so called "differentiable manifold").

Hereinafter, referring to the series of FIGS. 8-9, a computer system and a method for predicting a target outcome expected for a target positional value in a geographical data analysis system according to other exemplary embodiment of the present invention is described. In the following embodiment, the positional value is a geographical point (x, y) representing a location, each label represents an object, and the target outcome is estimated as a probability that a target result is obtained at a target location. Note that the object may represent a thing, a matter, a facility, a building, a vehicle, a person or a creature, a plant, to name but a few.

Figure 8:
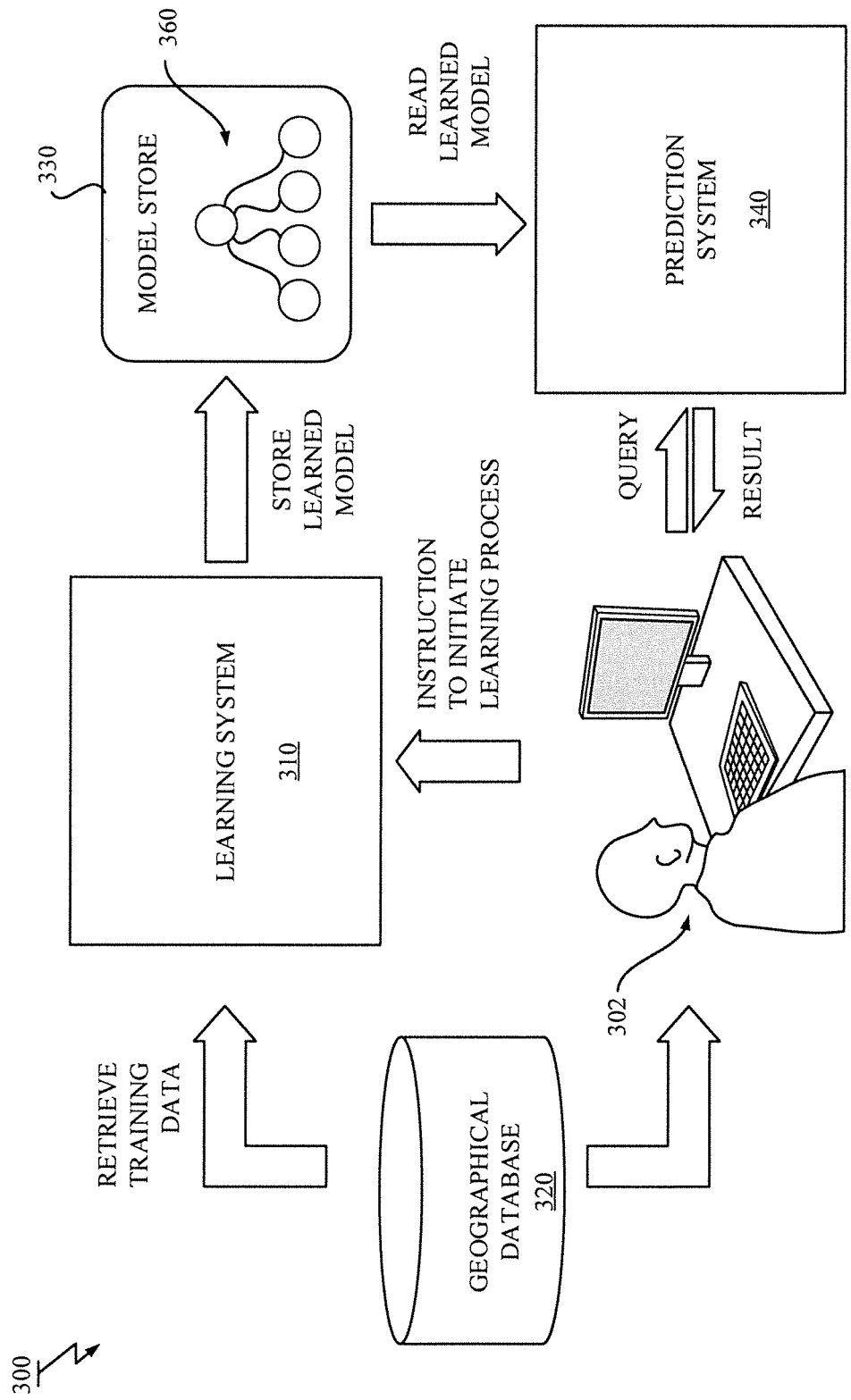
FIG. 8 illustrates a block diagram of a geographical data analysis system according to other exemplary embodiment of the present invention.

With reference to FIG. 8, a block diagram of a geographical data analysis system 300 is described. As shown in FIG. 8, the geographical data analysis system 300 may include a learning system 310 for learning a machine learning model; a geographical database 320 for storing a collection of geographical data; a model store 330 for storing the machine learning model trained by the learning system 310; and a prediction system 340 for predicting an outcome expected for a particular location by using the machine learning model that may be stored in the model store 330. In the described embodiment, the machine learning model that is trained by the learning system 310 and used by the prediction system 340 is a regression model 360 as similar to the aforementioned embodiment.

The geographical database 320 may store a collection of data records on one or more storage media or devices. Each data record may have a geographical point (x, y) representing a location and an attribute related to the location.

Figure 9:
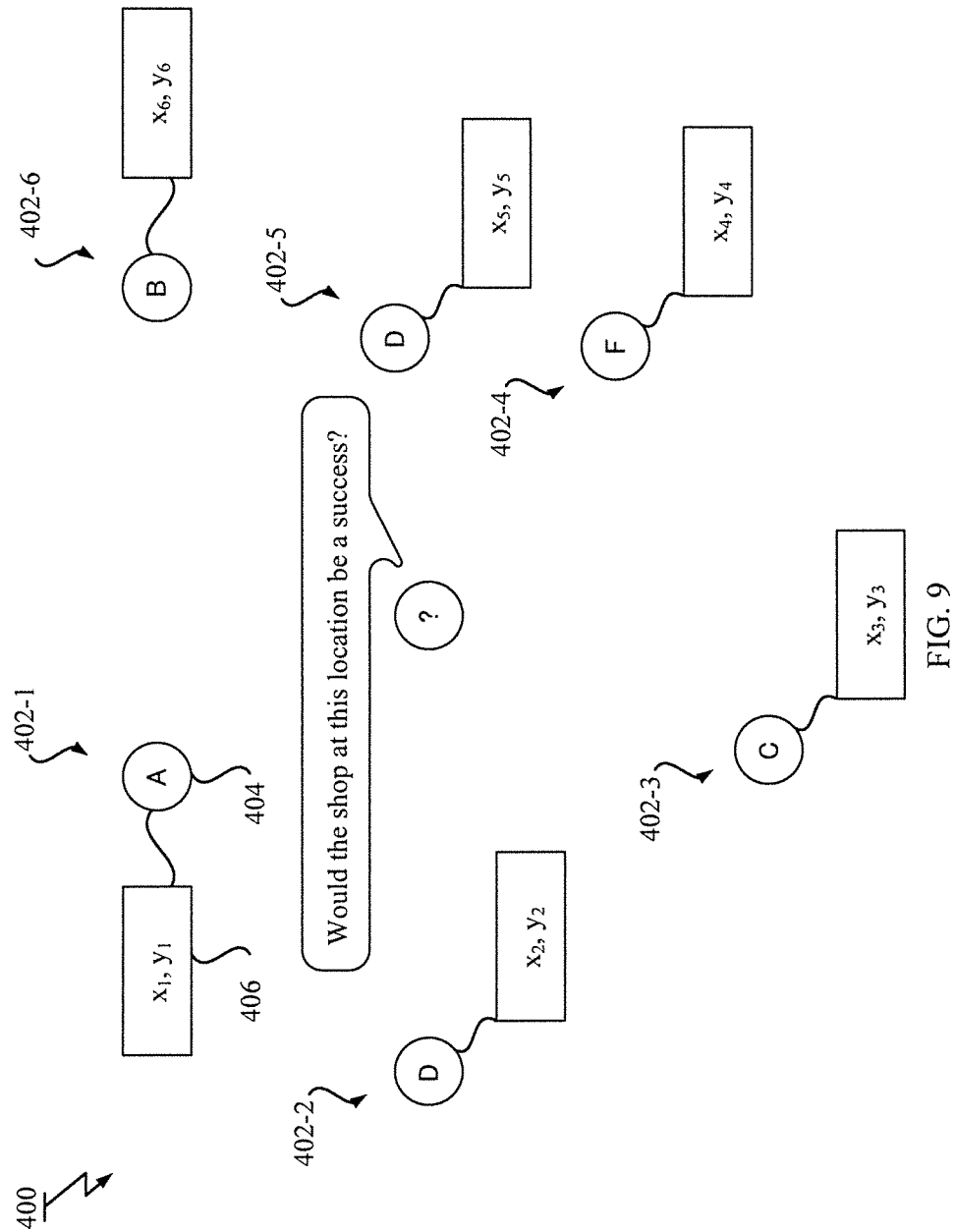
FIG. 9 shows data structure of geographical data managed in the geographical data analysis system and a question that the system tries to answer according to the other exemplary embodiment of the present invention.
Figure 10:
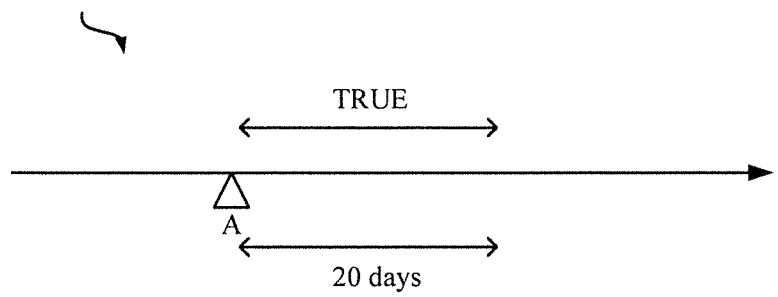
FIG. 10 shows conditions to be revealed, behind generation of events.
Figure 10:
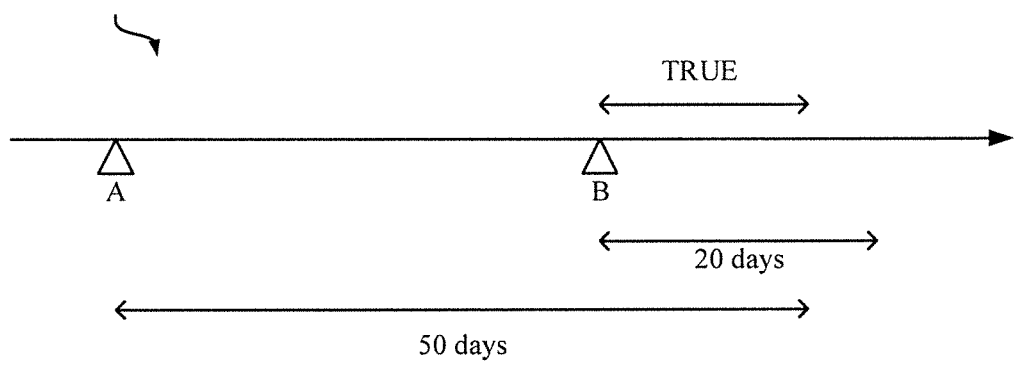
Figure 10:
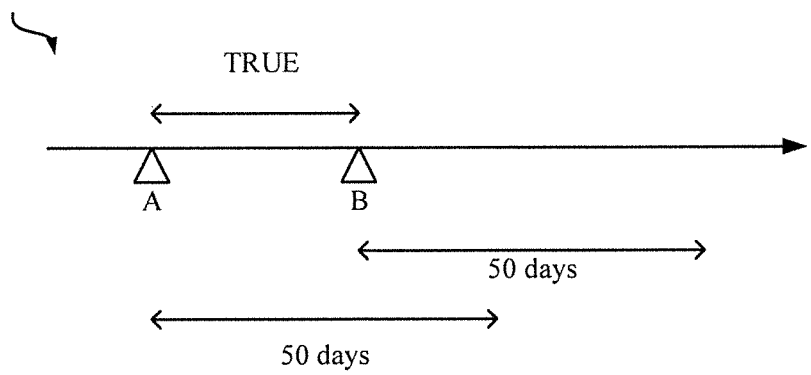

With reference to FIG. 9, an example of a data structure of geographical data stored in the geographical database 320 is depicted. As shown in FIG. 9, the geographical data 400 has a set of data records 402 (e.g., 402-1, 402-2, . . . , 402-6), each of which has a label 404 representing an object and a geographical point 406 representing a location related to the object. The geographical point 406 is a kind of positional information, and used as a positional value in the described embodiment. A predetermined label set is given for the system 300 and the label 404 contained in each data record 402 is one in the predetermined label set.

The label 404 is any type data that can represent a particular object. The specific label may depend on a domain or application, for which the geographical data 400 is used. Let consider a prediction of store development as an example, the label may be a value "post office", "hospital", "fire station", "elementary school", etc., in the case where the value describes type of the object. The label may be a key-value pair "building=post office", "building=hospital", etc., in the case where the key describes a category of an object and the key-value pair describes whole type of the object. Also the label may be a key "apartment" that is associated with a certain value that represents degree or quantity related to the key (e.g. "low-rise" or "60 floors") in the case where the key describes type of the object together with the value. A set of data records in a certain range may constitute geographical data to be used.

Referring back to FIG. 8, the learning system 310 is configured to train a regression model 360 by using a collection of training data. The learning system 310 may be configured to receive an instruction for initiating a learning process of the regression model 360 from an operator 302. In response to receiving the instruction, the learning system 310 may first retrieve a collection of training geographical data stored in the geographical database 320, which may be designated by the instruction, to prepare a collection of training data.

The training data may be prepared for a particular target outcome, which may be designated by the instruction that includes a target label. For example, the target outcome may be a success of a shop. Each training data may include a set of data records each having a label and a geographical point $\{(l_1, (x_1, y_1)), \ldots, (l_m, (x_m, y_m)), \ldots, (l_M, (x_M, y_M))\}$, and a pair of an answer label $l^*$ and a target geographical point $(x^*, y^*)$, in which the answer label is identical to the target label ($l^*=l_o$) for the positive sample or is not identical to the target label ($l^{**} \neq l_o$) for the negative sample. For example, data records of buildings and facilities around each own managed shop may be prepared. In this case, each answer label may be a data record about an own managed shop, which may be a success or miss. The learning system 310 trains the regression model 360 for the particular target outcome by using the prepared training data.

Conversion from the set of the data records to the input vector in the learning system 310 and the prediction system 340 is similar to that shown in FIG. 4, except for that each element $u_n$ is associated with as a representative geographical point $s_n$ ($=(x_m, y_m)$) instead of the representative timestamp $s_n$ ($=t_m$). The geographical point $(x_m, y_m)$ obtained from one or more data records having the corresponding label $L_n$ in the set of the data records, is set as a representative geographical point $s_n$. In a particular embodiment, when the corresponding label $L_n$ appears more than one time, a geographical point $(x_m, y_m)$ closest to the target geographical point $(x^*, y^*)$ may be selected from among one or more data records having the corresponding label $L_n$. The representative geographical point $s_n$ represents locational relationship between a location for data records having the corresponding label ($l_m = L_n$, $(x_m, y_m)$) and a location represented by the target geographical point $(x^*, y^*)$.

The regression model 360 trained by the learning system 310 may be stored in the model store 330. The model store 330 may store the trained regression model 360 with their parameters in one or more storage media or devices.

A structure of the regression model 360 is similar to that shown in FIG. 5, except for that the input vector u is associated with the representative geographical points $s_n$ and the weight function $k_n$ has a different form.

As similar to the aforementioned embodiment, the function is represented by a product of the value of the element $u_n$ and a weight calculated by a weight function $k_n$. Each weight function $k_n$ (subsequently the function $f_n$) is parameterized by a weight parameter $w_n$ and a positional parameter $a_n$. In a particular embodiment, the weight function $k_n$ may be represented by following formula:

$$k_n(s_n) = \frac{w_n}{1 + e^{|(x_n, y_n) - (x^*, y^*)| - a_n}},$$

where the weight function $k_n$ is close to $w_n$ for $|(x_n, y_n) - (x^*, y^*)| < a_n$ and close to 0 for $|(x_n, y_n) - (x^*, y^*)| > a_n$. In a particular embodiment, it is preferable that polarity of monotonicity of the function $f_n$ ($=u_n \cdot k_n$) for each parameter does not change according to the other parameters. Thus, the weight function $k_n$ can be represented by a 4-parameter function expressed as follow:

$$k_n(s_n) = \frac{w_{n+}}{1 + e^{|(x_n, y_n) - (x^*, y^*)| - a_{n+}}} + \frac{w_{n-}}{1 + e^{|(x_n, y_n) - (x^*, y^*)| - a_{n-}}},$$

where $w_{n+} > 0$, $w_{n-} < 0$, $a_{n+} > 0$, and $a_{n-} > 0$.

In the described embodiment, the weight function $k_n$ is a kind of a bump function that has monotonicity to the distance between the target geographical point and the representative geographical point ($|(x_n, y") - (x^*, y^*)|$), which represents an assumption that the influence from the label $L_n$ has just one peak in space. Thus, a closer object makes a stronger influence on other object. The output function may be same as the aforementioned embodiment.

The prediction system 340 is configured to estimate a probability that the target outcome is obtained at a target location from an input set by using the regression model 360 that has been already trained by the learning system 310. The prediction system 340 may be configured to receive a query from an operator 302 to perform a prediction process. The query may include or specify geographical data to be used and a target geographical point that represents the target location for analysis. An input set of data records each having a label and a geographical point is prepared from the given geographical data. For example, data records of buildings and facilities around one potential location to consider opening a new store may be prepared.

The prediction system 340 reads the regression model 360 from the model store 330, inputs the give input set to the regression model 360 to estimate the probability of the target outcome expected for the target location and returns a result for the query to the operator 302.

Note that the regression model 360 employed in the described embodiment can be seen as an extension of a binary logistic regression model where a binary dependent variable is used and a sigmoid function is used as the output function, With reference to FIG. 9, a question that the geographical data analysis system 300 tries to answer is also illustrated. The prediction in the described embodiment is a task to answer a question like "Would the shop at particular location be a success?". However, in other embodiment, the regression model 360 can be modified to an extension of a multiple regression model where a continuous dependent variable is used. In this embodiment, the target outcome is estimated as an estimated value of an evaluation item for the target location. The prediction system 340 may try to answer a question like "What is the anticipated sales amount when the new shop is opened at the particular location?". Also, representation of location is not limited to a two-dimensional geographical point. The location can be represented by three-dimensional coordinate point.

Flowcharts of a learning process and a prediction process according to the other exemplary embodiment of the present invention is almost the same as that of the aforementioned exemplary, embodiment Advantage of Novel Learning Model According to the aforementioned embodiments, it is possible to predict the target outcome expected for the target positional value efficiently with taking positional information obtained from the data records into account. Preferably, it is possible to suppress the increase in the complexity of the learning model.

By introducing the positional parameter $a_n$ in addition to the weight parameter $w_n$, the scale of the influence from the corresponding label $L_n$ (e.g., event or object) can be incorporated into the learning model. Since the scale of the influence from the corresponding label $L_n$ can be incorporated into the learning model and is determined as the trained positional parameter $a_n$ in the learning model, designation of the scale for each label $L_n$ before analysis can be made unnecessary. Thus, there is no or little need for analysts to have knowledge about the scale of the influence from the labels in advance.

With respect to analysis that can consider temporal scale, RNNs (Recurrent Neural Networks) and LSTMs (Long short-term memories) are known. However, these technologies may use a predefined scale in time dimension; in which a discrete temporal scale parameter is assumed. Also, these technologies have larger expressive power, but along with that, the complexity of the model is drastically increased.

The complexity of a space of functions that can be learned by a statistical algorithm may be measured by the VC (Vapnik-Chervonenkis) dimension of the hypothesis space, which gives the theoretical bound of the cost of the learning. The VC dimension of the set of mappings from R to [0, 1] is known to be infinity. Even when the function space is limited to the linear sum of predefined linearly independent functions, the VC dimension can still be the number of the predefined functions at the maximum. On the other hand, the VC dimension of a set of functions $\{F_v(z)|$ v is a real value of one parameter; z denotes a variable$\}$ that satisfies;

$$v_1 <= v_2 \rightarrow F_{v_1}(z) <= F_{v_2}(Z),$$

which represents monotonicity of the function to the parameter v, is merely one. The same may hold for the metric space with higher dimensions such as geographic data (dimension=2) and 3D spatial data (dimension=3). When combined with the weight parameter (e.g., equation (1)), the VC dimension can be more than 2 (e.g. 4 or 5), which is better than infinity and the number of the predefined functions.

Therefore, the monotonicity of the function $f_n$ to the positional parameter $a_n$ makes it easier for the parameters to converge to an optimal solution. If the function $f_n$ is monotonic to the positional parameter $a_n$, regardless of the point along the positional axis (e.g., time or spatial axis) at which the sample is positioned, the change direction of the positional parameter $a_n$ (whether the positional parameter $a_n$ is to be increased or to be decreased) when comparing the actual value and the target value of the function $f_n$ is unchanged. Therefore, it becomes easy to tune the positional parameter $a_n$.

Meanwhile, the monotonicity of the function to the difference or distance between the representative positional value $s_n$ and the target positional value *t (or (x*, y*)) represents an assumption that the influence from the label is monotonic in time or space, or an assumption that the influence from the label has just one peak in a space or time, respectively. When considering temporal or spatial influence by using a monotonically decreasing function of the difference or the distance, it is possible to parameterize the range of the influence and to avoid increasing parameters along the positional axis (time or spatial axis). Also, when such a function and parameters are set, the function would easily satisfy the monotonicity in the aforementioned sense. Thus, by assuming the monotonicity of the function $f_n$ to the difference or the distance, the number of the parameters can be drastically reduced and search the space of parameters can be narrowed down to a range that matches the reality. One or several parameters are practically sufficient for one label. Thereby, the number of the parameters in the learning model is almost linear to the number of the labels in the label set.

Furthermore, since the increase in the complexity of the learning model can be suppressed, rapid learning of the learning model is possible. In the other words, the amount of training data required for learning can be reduced.

A program implementing the event sequence analysis system 100 shown in FIG. 1 and the learning process and the prediction process shown in FIG. 6 and FIG. 7 according to the exemplary embodiment was coded and executed for several synthesized event sequence data, where one event sequence data has ten events with labels randomly generated from a predetermined label set L (={A, B, . . . , J}) and time intervals set by uniform distribution. For each training event sequence data, an answer label l* (=True/False) at randomly selected timestamp t* was given in a manner based on one of three conditions (1)-(3) shown in FIG. 10, each of which is a condition to be revealed, behind generation of events. The event sequence data had a positive answer label l* (=True) when the randomly selected timestamp t* satisfied a given condition under the given events. The event sequence data had a negative answer label l* (=False) when the randomly selected timestamp t* did not satisfy the given condition under the given events. For each test event sequence data, a randomly selected target timestamp t* was given.

As for examples, the regression model shown in FIG. 5 was trained for each condition by using the training data having a size of 10,000 samples with 100 epochs. The gradient method with cross-entropy cost function was used. As for options for the gradient method, L2 regularization and AdaGrad were employed. Note that the strength of the regularization constraint for the weight parameters $w_n$ was different from that for the positional parameters $a_n$. As for comparative examples, a standard binary logistic regression model was trained. The training condition for the comparative examples, including the training data size and the number of the epochs, was identical to that for the examples.

In the examples, after the learning process of the regression model was completed, the network structure from the input layer to the output layer with trained parameters was stored. Then, accuracies of the trained regression models of the examples and the logistic regression model of the comparative examples were evaluated for test event sequence data with a size of 1,000 samples using F-measure. The evaluated results of the examples and the comparative examples are summarized as follow:

| Conditions | (1) | (2) | (3) |
| --- | --- | --- | --- |
| Comparative examples | 69.5% | 72.0% | 71.2% |
| Examples | 99.5% | 95.7% | 92.6% |

As shown in the aforementioned table, the trained regression model of the examples marked high F-measures close to 100%, which is theoretically impossible for conventional logistic regression. It was demonstrated that the regression model of the examples can learn a condition that the target event (label) occurs in specific intervals from some events in the sense that the hypothesis space contains these conditions.

Figure 11:
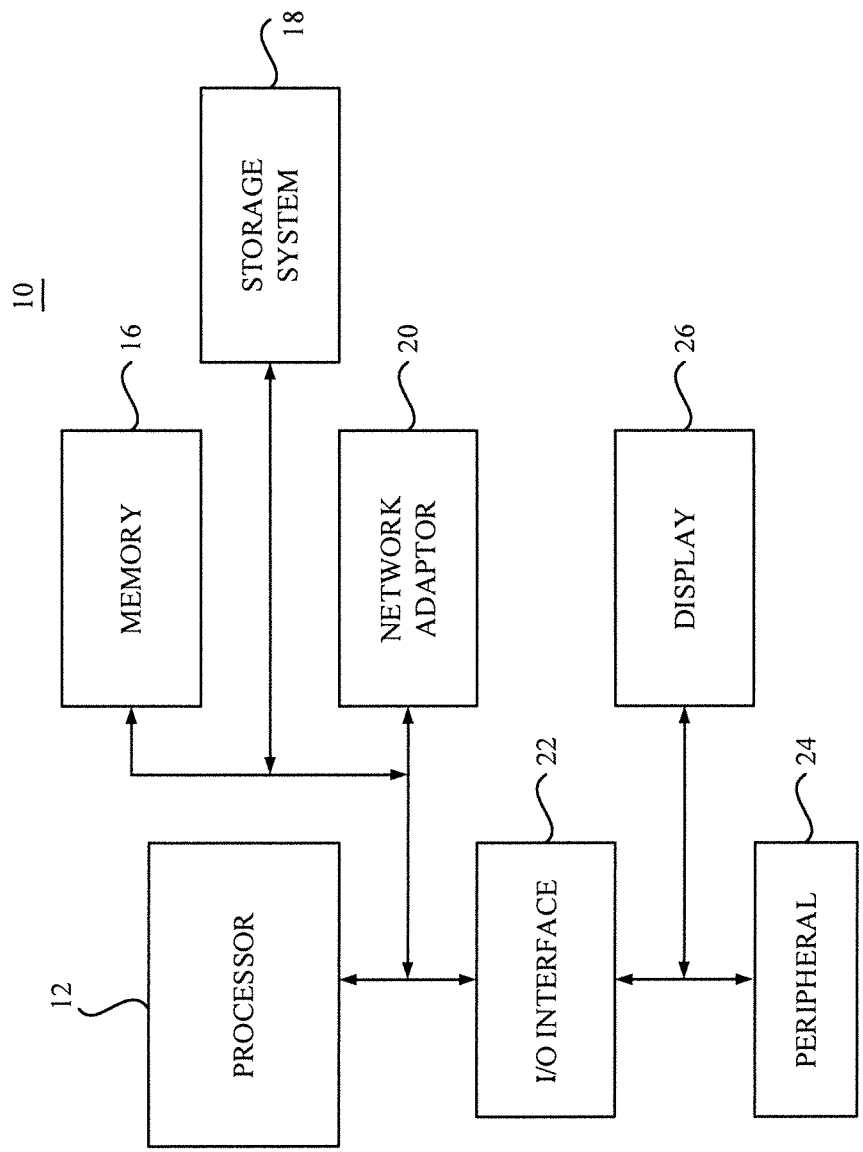
FIG. 11 depicts a computer system according to one or more embodiments of the present invention.

Referring now to FIG. 11, a schematic of an example of a computer system 10, which can be used for the event sequence analysis system 100 or the geographical data analysis system 300, is shown. The computer system 10 shown in FIG. 11 is implemented as a computer system. The computer system 10 is only one example of a suitable processing device and is not intended to suggest any limitation as to the scope of use or functionality of embodiments of the invention described herein. Regardless, the computer system 10 is capable of being implemented and/or performing any of the functionality set forth hereinabove.

The computer system 10 is operational with numerous other general purpose or special purpose computing system environments or configurations. Examples of well-known computing systems, environments, and/or configurations that may be suitable for use with the computer system 10 include, but are not limited to, personal computer systems, server computer systems, thin clients, thick clients, handheld or laptop devices, in-vehicle devices, multiprocessor systems, microprocessor-based systems, set top boxes, programmable consumer electronics, network PCs, minicomputer systems, mainframe computer systems, and distributed cloud computing environments that include any of the above systems or devices, and the like.

The computer system 10 may be described in the general context of computer system-executable instructions, such as program modules, being executed by a computer system. Generally, program modules may include routines, programs, objects, components, logic, data structures, and so on that perform particular tasks or implement particular abstract data types.

As shown in FIG. 11, the computer system 10 is shown in the form of a general-purpose computing device. The components of the computer system 10 may include, but are not limited to, a processor (or processing unit) 12 and a memory 16 coupled to the processor 12 by a bus including a memory bus or memory controller, and a processor or local bus using any of a variety of bus architectures.

The computer system 10 typically includes a variety of computer system readable media. Such media may be any available media that is accessible by the computer system 10, and it includes both volatile and non-volatile media, removable and non-removable media.

The memory 16 can include computer system readable media in the form of volatile memory, such as random access memory (RAM). The computer system 10 may further include other removable/non-removable, volatile/non-volatile computer system storage media. By way of example only, the storage system 18 can be provided for reading from and writing to a non-removable, non-volatile magnetic media. As will be further depicted and described below, the storage system 18 may include at least one program product having a set (e.g., at least one) of program modules that are configured to carry out the functions of embodiments of the invention.

Program/utility, having a set (at least one) of program modules, may be stored in the storage system 18 by way of example, and not limitation, as well as an operating system, one or more application programs, other program modules, and program data. Each of the operating system, one or more application programs, other program modules, and program data or some combination thereof, may include an implementation of a networking environment. Program modules generally carry out the functions and/or methodologies of embodiments of the invention as described herein.

The computer system 10 may also communicate with one or more peripherals 24 such as a keyboard, a pointing device, an audio system, etc.; a display 26; one or more devices that enable a user to interact with the computer system 10; and/or any devices (e.g., network card, modem, etc.) that enable the computer system 10 to communicate with one or more other computing devices. Such communication can occur via Input/Output (I/O) interfaces 22. Still yet, the computer system 10 can communicate with one or more networks such as a local area network (LAN), a general wide area network (WAN), and/or a public network (e.g., the Internet) via the network adapter 20. As depicted, the network adapter 20 communicates with the other components of the computer system 10 via bus. It should be understood that although not shown, other hardware and/or software components could be used in conjunction with the computer system 10. Examples, include, but are not limited to: microcode, device drivers, redundant processing units, external disk drive arrays, RAID systems, tape drives, and data archival storage systems, etc.

The present invention may be a computer system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components and/or groups thereof.

The corresponding structures, materials, acts, and equivalents of all means or step plus function elements in the claims below, if any, are intended to include any structure, material, or act for performing the function in combination with other claimed elements as specifically claimed. The description of one or more aspects of the present invention has been presented for purposes of illustration and description, but is not intended to be exhaustive or limited to the invention in the form disclosed.

Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method for training a learning model to predict an outcome expected for a particular positional value, the method comprising:
    obtaining an input set of data records and a target positional value, each data record having a label and a positional value, the label of each data record being one in a label set; and
    training a logistic regression model including an output layer, an input layer corresponding to the label sets and a network structure provided therebetween, the network structure having a plurality of functions trained so as to evaluate influence from each label in the label set depending on a relationship between the target positional value and a representative positional value associated with the label in the label set, each of the plurality of functions including a weight function that takes the representative positional value, the target positional value, and a positional parameter as an input, and the output layer having an output function that receives a sum of outputs from the plurality of functions to estimate a target output.

2. The method of claim 1, wherein the method further comprises:
    generating an input vector for the logistic regression model from the input set, the input vector including a plurality of elements each having a value representing at least whether a corresponding label in the label set is observed in the input set or not, each element being associated with a positional value obtained from one or more data records having the corresponding label in the input set as the representative positional value.

3. The method of claim 1, wherein each function is parameterized by a positional parameter and a weight parameter for a corresponding label in the label set, the positional parameter representing a range of influence from the corresponding label on a target outcome, the weight parameter representing a magnitude of the influence from the corresponding label on the target outcome.

4. The method of claim 3, wherein each function is monotonic to the positional parameter.

5. The method of claim 3, wherein the relationship is a difference or distance between the representative positional value and the target positional value, and each function is monotonic to the difference or the distance.

6. The method of claim 4, wherein the polarity of monotonicity of each positional parameter does not depends on the corresponding weight parameter.

7. The method of claim 1, wherein each positional value and the target positional value represent a time and a target time, respectively, each label represents an event, and a target outcome is estimated as a probability that a target event is observed at the target time.

8. The method of claim 1, wherein each positional value and the target positional value represent a location and a target location, respectively, each label represents an object, and a target outcome is estimated as a probability that a target result is obtained at the target location.

9. The method of claim 1, wherein each positional value and the target positional value represent a location and a target location, respectively, each label represents an object, and a target outcome is estimated as an estimated value of an evaluation item for the target location.

10. The method of claim 3, wherein the method further comprises:
    preparing a collection of training data, each training data including a set of data records each having a label and a positional value, a given positional value, and an answer given for the given positional value, the positional parameter and the weight parameter being trained by using the collection of the training data.

11. The method of claim 10, wherein the method further comprises:
    outputting the trained positional parameter as a range of the corresponding label to affect a target outcome.

12. The method of claim 10, wherein the method further comprises:
    estimating an outcome for the given positional value from the set of data records in one training data using the logistic regression model; and
    updating the positional parameter and the weight parameter by comparing the answer given for the given positional value with the outcome estimated for the given positional value.

13. The method of claim 12, wherein the weight parameter is updated under a regularization constraint having a strength different from the positional parameter.

14. The method of claim 1, wherein the output function is an inverse function of a link function and the link function is a logit function.

15. The method of claim 1, wherein the weight functions are expressed as:

$$k_n(s_n) = \frac{w_n}{1 + e^{t^* - s_n - a_n}},$$

where the $k_n$, is the weight function, $s_n$ is the representative position, $w_n$ is a magnitude of influence from a label on the target outcome, t* is a target timestamp, and $a_n$ is a positional parameter.

16. The method of claim 1, wherein the weight functions are expressed as:

$$k_n(s_n) = \frac{w_{n+}}{1 + e^{t^* - s_n - a_{n+}}} + \frac{w_{n-}}{1 + e^{t^* - s_n - a_{n-}}},$$

where the $k_n$, is the weight function, $s_n$ is the representative position, $w_{n+}$ is a positive magnitude of influence, $m_{n-}$ is a negative magnitude of influence, t* is a target timestamp, $a_{n+}$ is a positive positional parameter, and $a_{n-}$ is a negative positional parameter.

17. A computer-implemented method for training a learning model to predict an outcome expected for a particular positional value, the method comprising:
    obtaining an input set of data records and a target positional value, each data record having a label and a positional value;

generating an input vector from the input set, the input vector including a plurality of elements representing labels observed in the input set, the elements being associated with representative positional values; and training a logistic regression model to calculate a degree of influence from each label observed in the input set for the target positional value in a manner based, at least in part, on the elements and the representative positional values associated therewith, and to compute a target outcome for the target positional value based on the degree of influence from each label observed in the input set, where the logistic regression model includes a plurality of functions, each including a weight function that takes a respective representative positional value, the target positional value, and a positional parameter as an input, and the output layer having an output function that receives a sum of outputs from the plurality of functions to estimate a target output.

18. The method of claim 17, wherein each element has a value representing at least whether a corresponding label is observed in the input set or not, each representative positional value associated with the corresponding label being selected from among one or more data records having the corresponding label in the input set, the degree of influence from one label being evaluated by a function parameterized by a positional parameter and a weight parameter, the positional parameter representing a range of the degree of influence from the one label on the target outcome, the weight parameter representing a magnitude of influence from the one label on the target outcome.

19. A computer-implemented method for learning a learning model used for predicting an outcome expected for a particular positional value, the method comprising:

preparing a collection of training data each including a set of data records, a given positional value and an answer given for the given positional value, each data record having a label and a positional value, the label of each data record being one in a label set;

initializing a logistic regression model including an output layer, an input layer corresponding to the label set and a network structure provided therebetween, the network structure having a plurality of functions to evaluate influence from each label in the label set depending on a relationship between the given positional value and a representative positional value associated with the label in the label set, each of the plurality of functions including a weight function that takes the representative positional value, the given positional value, and a positional parameter as an input, and the output layer having an output function that receives a sum of outputs from the plurality of functions to estimate a target output;

estimating an outcome for the given positional value from the set of data records in each training data using the logistic regression model; and updating the plurality of the functions of the logistic regression model by comparing the answer in each training data with the outcome estimated for the given positional value.

20. The method of claim 19, wherein each function is parameterized by a positional parameter and a weight parameter for a corresponding label in the label set, the positional parameter representing a range of influence from the corresponding label on the outcome, the weight parameter representing a magnitude of the influence from the corresponding label on the outcome.

21. A computer system for training a learning model to predict an outcome expected for a particular positional value, comprising:

a memory tangibly storing program instructions; and a processor in communications with the memory for executing the program instructions, wherein the processor is configured to:

obtain an input set of data records and a target positional value, wherein each data record has a label and a positional value, and the label of each data record is one in a label set;

train a logistic regression model including an output layer, an input layer corresponding to the label set and a network structure provided therebetween, wherein the network structure has a plurality of functions trained so as to evaluate influence from each label in the label set depending on relationship between the target positional value and a representative positional value associated with each label in the label set, each of the plurality of functions including a weight function that takes the representative positional value, the target positional value, and a positional parameter as an input, and the output layer having an output function that receives a sum of outputs from the plurality of functions to estimate a target output; and estimate a target outcome for the target positional value from the input set using the logistic regression model.

22. The computer system of claim 21, wherein the computer system is further configured to:

generate an input vector for the logistic regression model from the input set, wherein the input vector includes a plurality of elements each having a value representing at least whether a corresponding label in the label set is observed in the input set or not, and each element is associated with a positional value obtained from one or more data records having the corresponding label in the input set as the representative positional value.

23. The computer system of claim 21, wherein each function is parameterized by a positional parameter and a weight parameter for a corresponding label in the label set, the positional parameter represents a range of influence from the corresponding label on the target outcome, and the weight parameter represents a magnitude of the influence from the corresponding label on the target outcome.

24. A computer program product for predicting an outcome expected for a particular positional value, the computer program product comprising a computer readable storage medium having program instructions embodied therewith, the program instructions executable by a computer to cause the computer to perform the method of claim 1.

* * * * *